US012582388B2

(12) United States Patent
Black et al.

(10) Patent No.: US 12,582,388 B2
(45) Date of Patent: Mar. 24, 2026

(54) SYSTEM AND APPARATUS FOR REMOTE INTERACTION WITH AN OBJECT

(71) Applicant: THE UNIVERSITY OF BRITISH COLUMBIA, Vancouver (CA)

(72) Inventors: David Gregory Black, Vancouver (CA); Septimiu Salcudean, Vancouver (CA); Yas Oloumi Yazdi, West Vancouver (CA); Amir Hossein Hadi Hosseinabadi, Mountain View, CA (US)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 18/027,610

(22) PCT Filed: Jul. 15, 2022

(86) PCT No.: PCT/CA2022/051108
§ 371 (c)(1),
(2) Date: Apr. 19, 2024

(87) PCT Pub. No.: WO2023/000085
PCT Pub. Date: Jan. 26, 2023

(65) Prior Publication Data
US 2024/0173018 A1     May 30, 2024

Related U.S. Application Data

(60) Provisional application No. 63/224,646, filed on Jul. 22, 2021.

(51) Int. Cl.
| | |
|---|---|
| *G06F 3/01* | (2006.01) |
| *A61B 8/00* | (2006.01) |
| *G16H 40/67* | (2018.01) |

(52) U.S. Cl.
CPC ............ *A61B 8/565* (2013.01); *A61B 8/4245* (2013.01); *A61B 8/461* (2013.01); *G06F 3/016* (2013.01); *G16H 40/67* (2018.01)

(58) Field of Classification Search
None
See application file for complete search history.

(56) References Cited

U.S. PATENT DOCUMENTS

| | | | |
|---|---|---|---|
| 5,806,521 A * | 9/1998 | Morimoto | .............. A61B 8/463 |
| | | | 600/447 |
| 10,636,323 B2 | 4/2020 | Buras et al. | |

(Continued)

FOREIGN PATENT DOCUMENTS

| | | |
|---|---|---|
| WO | 2019165044 A1 | 8/2019 |
| WO | 2021191598 A1 | 9/2021 |

OTHER PUBLICATIONS

Abolmaesumi et al., "Image-Guided Control of a Robot for Medical Ultrasound", IEEE Transactions on Robotics and Automation, 2002, vol. 18(1), pp. 11-23.

(Continued)

*Primary Examiner* — Carl Adams
(74) *Attorney, Agent, or Firm* — Borden Ladner Gervais LLP; Geoffrey deKleine

(57) ABSTRACT

An apparatus for remote interaction with an object includes a local system and a remote system. The local system includes a mixed reality headset configured to display a virtual representation of a physical element relative to the object, and a device configured to obtain information relating to or dependent on position and orientation of the physical element interacting with the object. The remote system includes an electronic device including a display for displaying an image based on the information, and an input device for remote user interaction and configured to control position and orientation of the virtual representation dis- (Continued)

played on the mixed reality headset. The remote system is configured to communicate with the local system with latency of 0.5 seconds or less, facilitating alignment of the physical element with the position and orientation of the virtual representation.

13 Claims, 11 Drawing Sheets

(56) References Cited

U.S. PATENT DOCUMENTS

| | | | |
|---|---|---|---|
| 10,702,242 | B2 | 7/2020 | De Jonge et al. |
| 10,893,850 | B2 | 1/2021 | Gafner et al. |
| 2013/0237811 | A1 | 9/2013 | Mihailescu et al. |
| 2017/0007202 | A1* | 1/2017 | Peszynski ................ A61B 8/54 |
| 2017/0181726 | A1 | 6/2017 | Schneider et al. |
| 2019/0117190 | A1* | 4/2019 | Djajadiningrat ...... G06T 19/006 |
| 2019/0239850 | A1 | 8/2019 | Dalvin et al. |
| 2019/0261957 | A1 | 8/2019 | Zaslavsky et al. |
| 2020/0069291 | A1 | 3/2020 | Zaslavsky |
| 2020/0117898 | A1 | 4/2020 | Tian et al. |
| 2020/0214672 | A1 | 7/2020 | De Jonge et al. |
| 2020/0214682 | A1 | 7/2020 | Zaslavsky et al. |

OTHER PUBLICATIONS

Anderson et al., "Bilateral Control of Teleoperators with Time Delay", IEEE Transactions on Automatic Control, 1989, vol. 34 (5), pp. 494-501.

Boniface et al., "Tele-Ultrasound and Paramedics: Real-Time Remote Physician Guidance of the Focused Assessment With Sonography for Trauma Examination", Elsevier, 2011, vol. 29, pp. 477-481.
International Patent Application No. PCT/CA2022/051108, International Search Report and Written Opinion dated Oct. 18, 2022.
Korte et al., "Determining the Threshold of Time-Delay for Teleoperation Accuracy and Efficiency in Relation to Telesurgery", Telemedicine and e-Health, 2014, vol. 20 (12), pp. 1078-1086.
Madder et al., "Network Latency and Long-Distance Robotic Telestenting: Exploring the Potential Impact of Network Delays on Telestenting Performance", Catheterization and Cardiovascular Interventions, 2019, vol. 95(5) pp. 914-919.
Niemeyer et al., "Stable Adaptive Teleoperation", IEEE Journal of Oceanic Engineering, 1991, vol. 16(1), pp. 152-162.
Niemeyer et al., "Towards Force-Reflecting Teleoperation Over the Internet", Proceedings of the 1998 IEEE International Conference on Robotics Automation, 1998, pp. 1909-1915.
Meyres et al., "A Tele-Operated Robotic System for Mobile Tele-Echography: The Otelo Project: M-Health Emerging Mobile Health Systems", Topics in Biomedical Engineering, 2006, pp. 1-619.
Ye et al., "Improving Trajectory Tracking in Wave-Variable-Based Teleoperation", IEEE/ASME Transactions on Mechatronics, 2010, vol. 15(2), pp. 321-326.
U.S. Appl. No. 18/125,085, Final office Action dated Aug. 15, 2025.

* cited by examiner

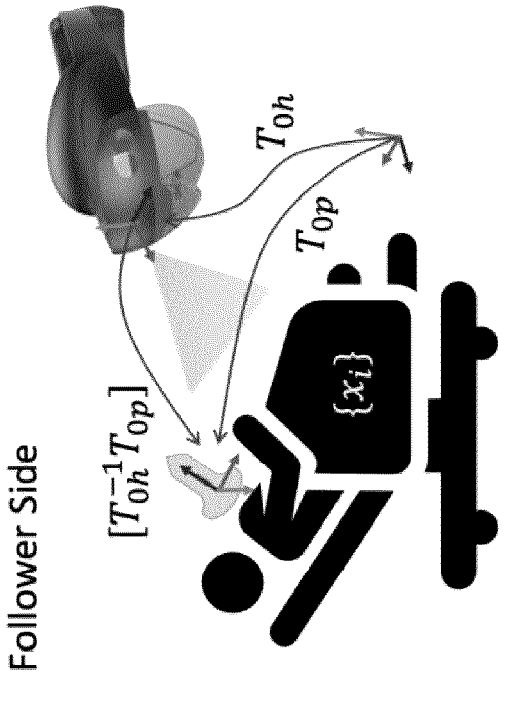
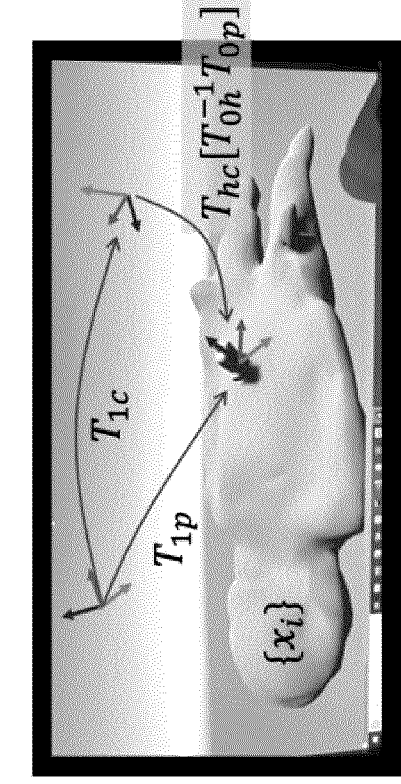
FIG. 9

FIG. 10A                    FIG. 10B

SYSTEM AND APPARATUS FOR REMOTE INTERACTION WITH AN OBJECT

FIELD OF TECHNOLOGY

The present disclosure relates to a method and apparatus for remote interaction with an object, for example, for remote sonography.

BACKGROUND

The fourth industrial revolution, or Industry 4.0, is expected to bring higher industrial performance and efficiency through the adoption of emerging technologies in robotics, artificial intelligence, cloud computing, and mixed reality. The same technologies are having an impact on healthcare and medicine. However, there is a disconnect between the technologies and their application. Many companies are unsure how to take advantage of Industry 4.0 to improve their business, while for many medical applications, the technology is not at a level where it can be used directly on patients, or the technology simply does not fit the application well.

One such problem is teleultrasound. In remote communities, access to expert care and diagnosis by sonographers is often severely lacking or infrequent. By enabling expert sonographers to remotely guide or teleoperate ultrasound (US) procedures in these communities, teleultrasound has immense potential to improve the quality of care of patients, both in rural regions and in ambulances. Teleultrasound may also decrease costs associated with transporting patients or medical workers, and increase safety in a pandemic such as COVID-19.

Ultrasound teleguidance systems have been implemented by numerous groups. For trauma patients, verbal guidance via radio while viewing a stream of the ultrasound images was explored by Boniface et al. (K. S. Boniface, H. Shokoohi, E. R. Smith, and K. Scantlebury, "Teleultrasound and paramedics: real-time remote physician guidance of the focused assessment with sonography for trauma examination," The American journal of emergency medicine, vol. 29, no. 5, pp. 477-481 2011). More modern systems sold by Clarius Mobile Health Corp. and Butterfly Network combine a mobile phone application with a wireless ultrasound transducer and remote access to the images and video conferencing via a cloud interface. However, in all these solutions the instructions for probe positioning, orientation, and force are given verbally or with augmented reality overlays of arrows or pointers. With these methods, a novice cannot perform the ultrasound probe positioning and orientation with low latency and high precision. The process itself relies on repeated communication between the expert and the novice and is very inefficient.

Robotic teleultrasound systems have also been developed which provide low latencies and high precision, as well as haptic feedback. These involve a robotic arm with ultrasound probe end effector which is teleoperated by a remote expert sonographer. Salcudean et al. presented a robot whose control was shared between the expert and a visual servoing system to maintain correct positioning on the carotid artery (P. Abolmaesumi, S. E. Salcudean, W.-H. Zhu, M. R. Sirouspour, and S. P. DiMaio, "Image-guided control of a robot for medical ultrasound," IEEE Transactions on Robotics and Automation, vol. 18, no. 1, pp. 11-23, 2002.). Another system, referred to as OTELO (P. Vieyres, G. Poisson, F. Courreges, N. Smith-Guerin, C. Novales, and P. Arbeille, "A tele-operated robotic system for mobile tele-echography:

The otelo project," in M-health. Springer, 2006, pp. 461-473.), has demonstrated clinical utility in trials. Recent work has even investigated the control of such systems over 5G and in the context of COVID-19. With robotic approaches, the expert has full control of the position of the ultrasound transducer and often has control over the applied force. The robot is capable of following the movement of the expert with low latency and high precision.

There are many drawbacks with robotic systems. While some are designed to be backdriveable and lightweight, issues of safe human-robot interaction and predictable and consistent autonomy remain unsolved. As a result, a human follower is still needed on-site to monitor the robot, and check and approve planned motion trajectories, limiting the efficiency of such systems. Furthermore, such robots have restricted workspaces, are time consuming to set up, too large to store on ambulances, and incongruously expensive compared to ultrasound systems. While ultrasound is usually an inexpensive procedure and is thus well suited to being a standard of care in remote communities, installing an expensive robot in every small town is not feasible.

Similar or related issues may also arise in other applications in which remote interaction with objects is desirable, for example, in other healthcare applications or in other applications, for example in non-destructive testing of objects.

Improvements in remote interaction with objects, for example, remote interaction of a doctor with a patient, are desirable.

SUMMARY

According to an aspect of an embodiment, an apparatus for remote interaction with an object is provided. The apparatus includes a local system that includes a mixed reality headset configured to display a virtual representation of a physical element relative to the object, and a device configured to obtain information relating to or dependent on position and orientation of the physical element interacting with the object. The apparatus also includes a remote system located remote from the object and in communication with the local system. The remote system includes an electronic device including a display for displaying an image based on the information relating to or dependent on the position and orientation of the physical element interacting with the object, and an input device for remote user interaction and configured to control position and orientation of the virtual representation displayed on the mixed reality headset. The remote system is configured to communicate with the local system with latency of 0.5 seconds or less, facilitating alignment of the physical element with the position and orientation of the virtual representation.

According to another aspect of an embodiment, a method of interaction with an object is provided. The method includes: establishing communication between a local system and a remote system located remote from the object; displaying on a mixed reality headset of the local system, a virtual rendering of a physical element positioned and oriented relative to the object; obtaining, by the local system, information relating to or dependent on position and orientation of the physical element interacting with the object; sending the information to the remote system; displaying, on a display of an electronic device of the remote system, the information relating to or dependent on the position and orientation of the physical element interacting with the object; receiving input at an input device of the remote system; and controlling position and orientation of the virtual rendering of the physical element, displayed on the mixed reality headset, relative to the object based on the input received at the input device of the remote system. The remote system communicates with the local system with latency of 0.5 seconds or less, facilitating alignment of the physical element with the position and orientation of the virtual rendering.

According to still another aspect of an embodiment, an apparatus for remote patient interaction is provided. The apparatus includes a local system that includes a mixed reality headset for displaying a virtual probe relative to a patient, and an ultrasound probe for locating relative to the patient to obtain signals for producing ultrasound images. The apparatus also includes a remote system located remote from the patient and in communication with the local system. The remote system includes an electronic device including a display for displaying an image including a position and orientation of the ultrasound probe relative to the patient and for displaying the ultrasound images produced utilizing signals from the ultrasound probe, and a haptic controller for remote user interaction and for controlling position and orientation of the virtual probe and for providing haptic feedback.

BRIEF DESCRIPTION OF THE DRAWINGS

Embodiments of the present disclosure will now be described, by way of example only, with reference to the attached Figures, in which:

FIG. 9 illustrates coordinate transforms for registration of the virtual ultrasound transducer to a patient and patient mesh in accordance with the example of FIG. 8;

FIG. 10A is a histogram showing latency for strong and weak 5G signals;

FIG. 10B is a histogram showing latency for local WiFi and 5G signals;

DETAILED DESCRIPTION

Figure 1:
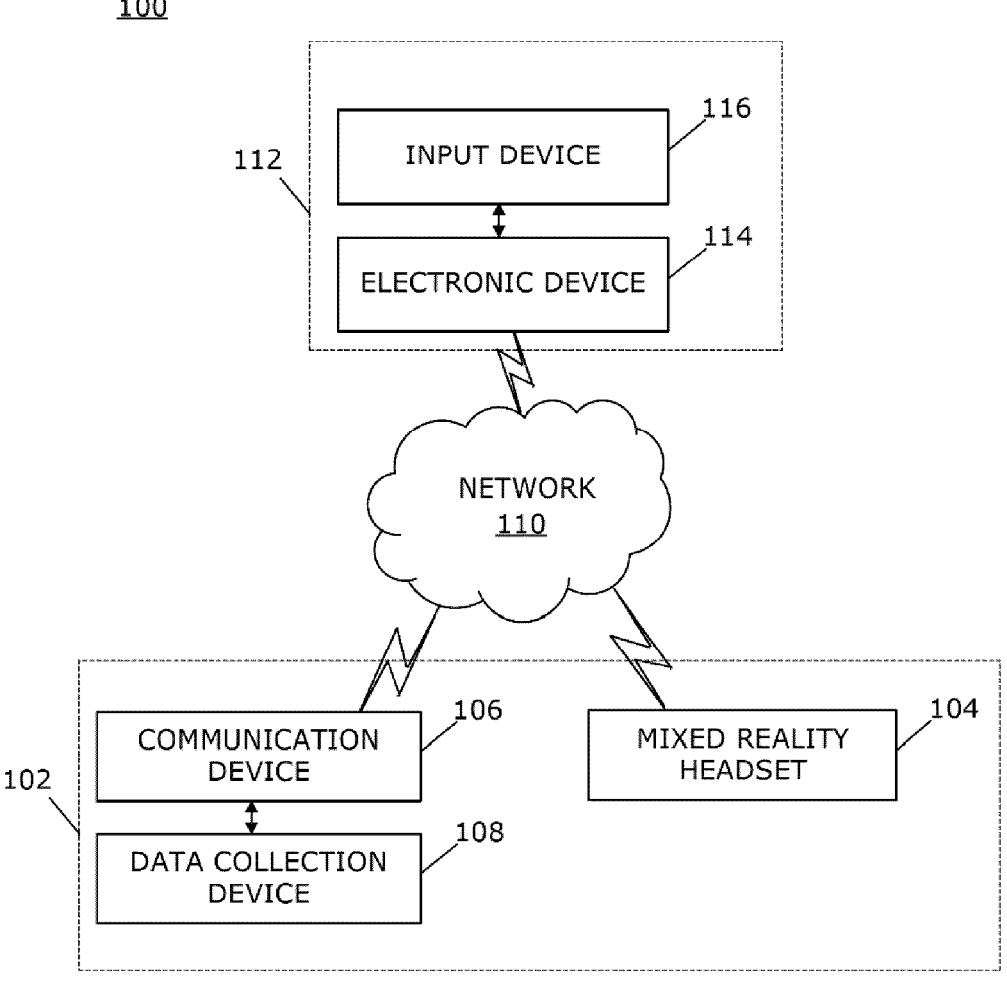
FIG. 1 is a block diagram of an apparatus for remote interaction including a local system and remote system in accordance with an aspect of an embodiment.

For simplicity and clarity of illustration, reference numerals may be repeated among the figures to indicate corresponding or analogous elements. Numerous details are set forth to provide an understanding of the examples described herein. The examples may be practiced without these details. In other instances, well-known methods, procedures, and components are not described in detail to avoid obscuring the examples described. The description is not to be considered as limited to the scope of the examples described herein.

The following describes an apparatus for remote interaction with an object. The apparatus includes a local system that includes a mixed reality headset configured to display a virtual representation of a physical element relative to the object, and a device configured to obtain information relating to or dependent on position and orientation of the physical element interacting with the object. The apparatus also includes a remote system located remote from the object and in communication with the local system. The remote system includes an electronic device including a display for displaying an image based on the information relating to or dependent on the position and orientation of the physical element interacting with the object, and an input device for remote user interaction and configured to control position and orientation of the virtual representation displayed on the mixed reality headset. The remote system is configured to communicate with the local system with latency of 0.5 seconds or less, facilitating alignment of the physical element with the position and orientation of the virtual representation.

A simplified block diagram of an example of an apparatus 100 for remote interaction with an object is shown in FIG. 1. The apparatus 100 includes a local system 102 located proximal to the object for physical interaction with the object.

The local system 102 includes a mixed reality headset 104 that is utilized to display a virtual element relative to the physical object. Thus, the mixed reality headset 104 is utilized to display virtual information overlaid on the physical environment that is visible through the mixed reality headset 104. The mixed reality headset may be any suitable mixed reality headset such as a Hololens 2™ available from Microsoft™. Thus, the mixed reality headset 104 may include a transparent or semi-transparent display through which the physical environment is visible. Alternatively, the mixed reality headset 104 may be a virtual reality headset or helmet that obtains images of the physical environment utilizing cameras of the virtual reality headset or helmet and displays the physical environment with virtual information overlaid.

The local system 102 also includes a communication device 106, such as a smartphone, notebook computer, tablet computer, mobile internet device, and so forth. The communication device 106 is connected to a data collection device 108. The data collection device 108 may be any suitable device or devices utilized to obtain information relating to or dependent on position and orientation of a physical element interacting with the object. For example, the data collection device 108 may be an ultrasound transducer that is housed in a physical body, referred to herein as an ultrasound probe. Thus, the ultrasound transducer is the data collection device. The physical element interacting with the object is the ultrasound probe that is utilized on the object, which may be a patient or may be an object for non-destructive testing.

Alternatively, the data collection device may be any other imaging device or any other measurement device or system such as an optical or electromagnetic tracking system, inertial measurement unit (IMU), stereo camera, force sensing arrangement, or temperature sensors. Thus, the ultrasound transducer is housed in the physical body that interacts with the patient. The transducer is utilized to collect ultrasound image data that is dependent on the position, orientation, and force of the ultrasound probe on the patient. The ultrasound image data is provided to the communication device 106. A visual image of the ultrasound transducer on the patient may also be provided utilizing a camera or vision system, which may be part of the mixed reality headset.

In another example, the physical element may be the body of a camera or an endoscope and the data collection device is the camera itself, which may be a lens, CMOS sensor and associated electronics. The image collected is the camera image and is a function of where the body of the camera is in relation to the patient.

In yet another example, the physical element may be a syringe that a local user positions to be coincident with a virtual rendering based on information from the remote system controlled by the remote user. The data collection device is a camera that captures images of the syringe relative to a patient.

The apparatus 100 also includes a remote system 112 located remote from the object. The remote system 112 is connected to the local system 102 by a network 110. The network 110 may include the internet and may include a cellular network in addition to the internet or as an alternative to the internet. Other communications may also be utilized, including for example, near field, Bluetooth®, WiFi, optical, radio, or a combination of communications. Alternatively, the network may be a local area network.

The remote system 112 includes an electronic device 114, which may be any suitable electronic device, including, for example, a personal computing device, a mobile computing device, a smart phone or any other suitable electronic device. The electronic device 114 includes a display for displaying an image based on the information relating to or dependent on the position and orientation of the physical element interacting with the object.

An input device 116 is connected to the electronic device 114, by wired or wireless connection. The input device 116 is utilized for remote user interaction and is connected to the local system 102 via the electronic device 114 connected to the network 110. The input device 116 controls the position and orientation of the virtual element displayed on the mixed reality headset 104, relative to the physical object, based on the remote user interaction. The input device 116 may be a haptic device such as a Touch X™ haptic device available from 3D Systems, Inc. Alternatively, the input device 116 may be, for example, a vision system, an electromagnetic sensing system, an optical infrared tracker, or a stereo camera system, for tracking position and orientation of another device or of a part of the user, such as the user's hands.

Figure 2:
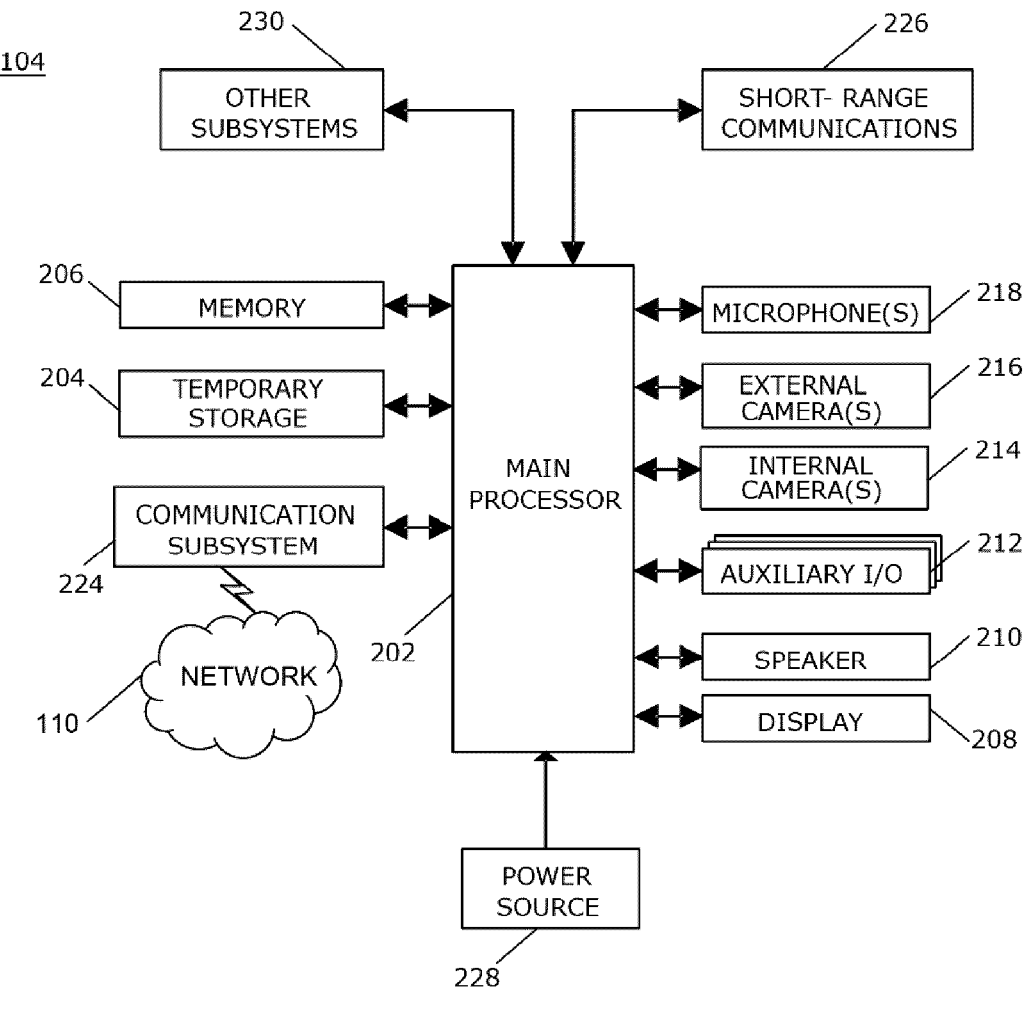
FIG. 2 is a block diagram illustrating a mixed reality headset of a local system in accordance with an aspect of an embodiment.

A simplified block diagram of an example of a mixed reality headset 104 of the local system 102 in accordance with an aspect of an embodiment is shown in FIG. 2. The mixed reality headset 104 includes multiple components, such as a main processor 202 that controls the overall operation of the mixed reality headset 104.

The main processor 202 interacts with other components of the mixed reality headset 104, including, for example, a temporary storage device 204, a memory 206, a display device 208, a speaker 210, an auxiliary input/output (I/O) subsystem 212, internal cameras 214, external cameras 216, one or more microphones 218, a communication subsystem 224, short-range communications 226, a power source 228, and, optionally, other subsystems 230.

The temporary storage device 204 may be, for example, Random Access Memory (RAM) that stores data that is processed by the main processor 202. The memory 206, such as flash memory, is utilized for persistent storage.

The mixed reality headset 104 provides augmented reality images or video output through the optical see-through display 208, which includes an interface, a controller and at least one display to display images. The images displayed may be an image in front of at least one of the user's eyes or may include a respective image in front of each one of the user's eyes. In addition to the display 208, output is provided via the speaker or speakers 210 or other audio output such as headphones or earphones. The auxiliary input/output (I/O) subsystem 212 includes an interface through which, for example, a USB controller or other peripheral device may be connected.

Input to the mixed reality headset 204 may be provided via the external cameras 216 mounted on the body of the mixed reality headset 204. The external cameras 216 may include multiple cameras to obtain images extending around the user, i.e., 360° around the user. The external cameras 216 may also include cameras to obtain images in an upward direction from the user, and in a downward direction from the user. Each of the external cameras 216 includes the functional components for operation of the camera, including the lens, the image sensor, and, optionally, a light sensor and light source, such as infrared light emitting diodes (LEDs). Thus, the external cameras 216 provide images of the user's environment or surroundings. The external cameras 216 may be one or more of visual light cameras, 3D sensing cameras, light field cameras, forward looking infrared cameras, near infrared cameras, ultraviolet cameras, or other imaging devices.

The terms upward and downward are utilized herein to generally describe direction of view of the external cameras 216 relative to the user when the mixed reality headset 104 is worn by the user and the user is in an upright position, and such terms are not otherwise limiting.

The one or more microphones, referred to herein as the microphone 218, may also be mounted in the body of the mixed reality headset 204 to provide input by converting audible information to electrical signals, which may be processed by the main processor 202 and may be transmitted to another electronic device to which the mixed reality headset 204 is coupled.

The one or more speakers 210 or other sound generators, referred to herein as the speaker or speakers 210, may also be mounted in the body of the mixed reality headset to provide sound.

The communication subsystem 224 receives signals from another electronic device and sends signals to the other electronic device to which the mixed reality headset 204 is coupled. Thus, for example, the signals from the microphone 218 or signals from the external cameras 216 may be sent via the communication subsystem 224. The communication subsystem 224 is also responsible for receiving signals from the other electronic device for processing by the main processor 202 to cause images, which may include video, to be displayed on the display 208 and for audio to be output through the speaker 210.

The mixed reality headset 104 optionally includes short-range communications 226 to perform various communication functions. For example, the mixed reality headset 104 may include Bluetooth, Bluetooth Low Energy (BLE) or infrared (IR) communications capability, for example, for communicating with a peripheral device or accessory.

The power source 228 may be one or more rechargeable batteries or a port to an external power supply to power the mixed reality headset 104.

The systems and subsystems that interact with the main processor 202 and are described herein are provided as examples only. Other subsystems 230 may also interact with the main processor 202.

Utilizing the images from the internal camera 214, the main processor 202 may be operable to track eye motion. Based on the eye motion tracking, the direction that the user is looking may be identified. The direction may be, for example, an angle or angles, such as angular offset or offsets from straight ahead. Thus, when a user glances upwardly, downwardly, or to either side, the direction is identified and the images displayed utilizing the display 208 may be changed or adjusted based on the direction.

Figure 3:
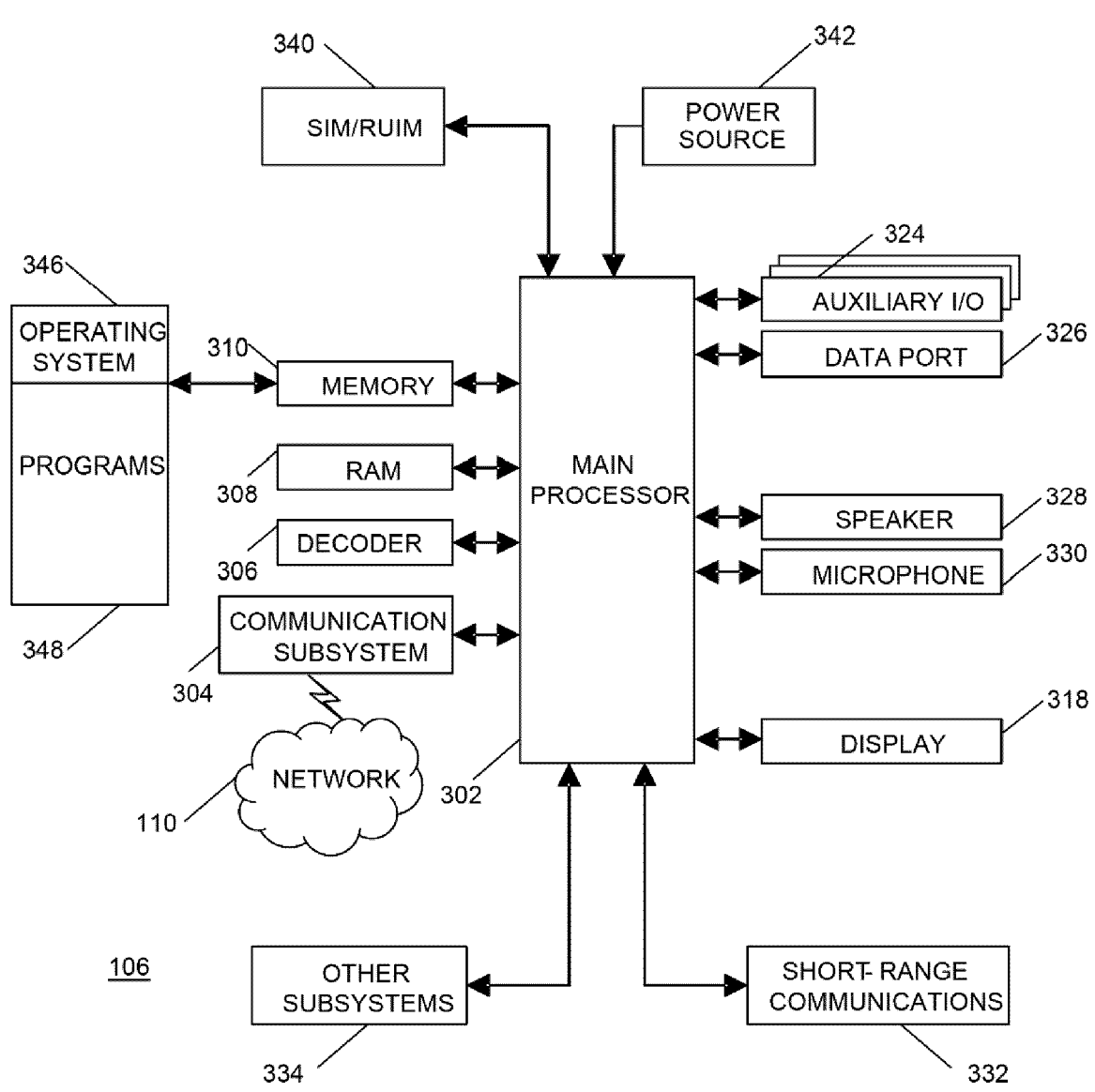
FIG. 3 is a block diagram of a communication device of a local system in accordance with an aspect of an embodiment.

A block diagram of one example of a communication device 106 is shown in FIG. 3. As indicated above, the communication device 106 may be, for example, a smartphone, notebook computer, tablet computer, mobile internet device, and so forth. In the present example, the communication device 106 is a portable electronic device. The communication device 106 includes multiple components, such as a processor 302 that controls the overall operation of the communication device 106. Communication functions, including data and voice communications, are performed through a communication subsystem 304. Data received by the communication device 106 is decompressed and decrypted by a decoder 306. The communication subsystem 304 receives messages from and sends messages to the network 110. A power source 342, such as one or more rechargeable batteries or a port to an external power supply, powers the communication device 106.

The processor 302 interacts with other components, such as a Random Access Memory (RAM) 308, memory 310, a display 318, an auxiliary input/output (I/O) subsystem 324, a data port 326, a speaker 328, a microphone 330, short-range communications 332 and other device subsystems 334. The speaker 328 is utilized to output audible signals. Although not shown, the processor may also interact with a loudspeaker, for example.

The display 318 may be a touch-sensitive display including touch sensors and controller for input to the processor 302. Information, such as text, characters, symbols, images, icons, and other items that may be displayed or rendered on a communication device 106, is displayed on the display 318 via the processor 302.

To identify a subscriber for network access, the communication device 106 may utilize a Subscriber Identity Module or a Removable User Identity Module (SIM/RUIM) card 344 for communication with a network, such as the network 110. Alternatively, user identification information may be programmed into memory 310.

The communication device 106 includes an operating system 346 and software programs, applications, or components 348 that are executed by the processor 302 and are typically stored in a persistent, updatable store such as the memory 310. Additional applications or programs may be loaded onto the communication device 106 through the network 110, the auxiliary I/O subsystem 324, the data port 326, the short-range communications subsystem 332, or any other suitable subsystem 334.

A received signal is processed by the communication subsystem 304 and input to the processor 302. The processor 302 processes the received signal for output to the display 318 and/or to the auxiliary I/O subsystem 324. Data may be transmitted over the network 110. For voice communications, the overall operation of the communication device 106 is similar. The speaker 328 outputs audible information converted from electrical signals, and the microphone 330 converts audible information into electrical signals for processing.

The communication device 106 is in communication with the data collection device 108, which may be any device for obtaining information relating to or dependent on position and orientation of a physical element interacting with the object. In the example of the ultrasound transducer utilized on a patient, the ultrasound probe that includes the ultrasound transducer may be in communication with the communication device 106 by wired connection to the communication device, via short-range communications, through the short-range communications subsystem 332, such as BLUETOOTH™ or WiFi, or any other suitable communication connection.

The ultrasound probe may include an array of transducers that are utilized to generate ultrasonic signals that are emitted from an end thereof. The ultrasound probe may include any suitable transducer such as one or more ceramic piezo transducers, Capacitive Micromachined Ultrasound Transducers (CMUTs), or Piezoelectric Micromachined Ultrasonic Transducers (PMUTs). When the ultrasonic signals are transmitted into the body, the signals hit tissue boundaries and some portion of the signals are reflected back to the ultrasound transducer while others proceed on through the body and reflect off of other tissue boundaries. The signals that are reflected back are dependent on the density and mechanical impedance of the tissue and the timing is dependent on depth. The signals are received at the ultrasound transducer and are used by a local processor or by a remote processor, via the communication device 106, for example, to form an ultrasound image that may be displayed on the display 318.

Figure 4:
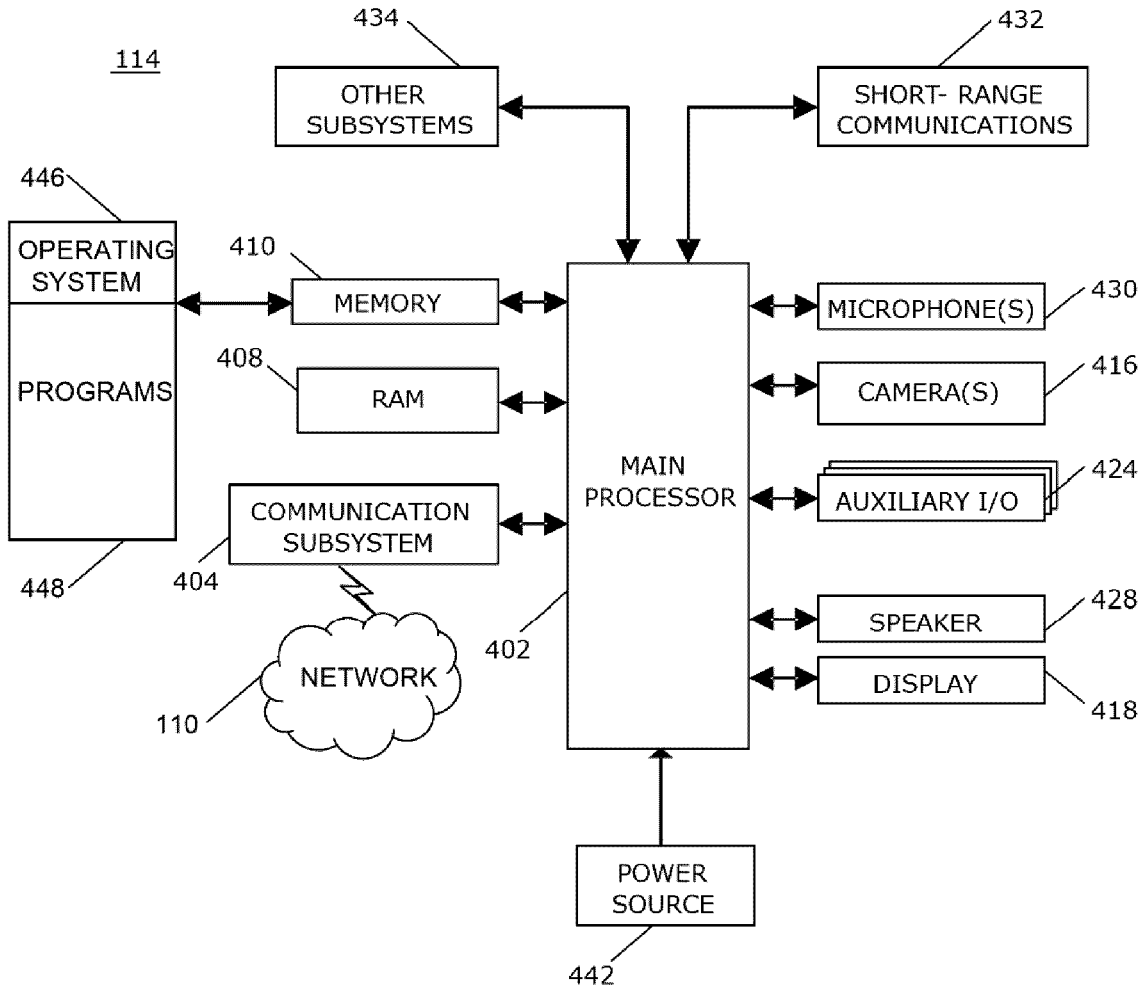
FIG. 4 is a block diagram of an electronic device of a remote system in accordance with an aspect of an embodiment.

Referring now to FIG. 4, a block diagram of one example of an electronic device 114 is shown. As indicated above, the electronic device 114 may be, for example, a desktop computer, notebook computer, tablet computer, smartphone, and so forth. Alternatively, the electronic device 114 may be or may comprise a mixed reality or virtual reality headset. In the present example, the electronic device 114 is a desktop computer. The electronic device 114 includes multiple components, such as a processor 402 that controls the overall operation of the electronic device 114. Communication functions, including data and voice communications, are performed through a communication subsystem 404. Data, including voice communications, is sent via the communication subsystem 404 connected to the network 110. A power source 442, such as a port to an external power supply or an internal battery, powers the electronic device 114.

The processor 402 interacts with other components, such as a Random Access Memory (RAM) 408, memory 410, one or more cameras 416, a display 418, an auxiliary input/output (I/O) subsystem 424, a speaker 428, a microphone 430, short-range communications 432 and other device subsystems 434. The speaker 428 is utilized to output audible signals. The auxiliary input/output (I/O) subsystem 424 may include a mouse, for example, for input.

The display 418 may be a touch-sensitive display including touch sensors and controller for input to the processor 402. Information, such as text, characters, symbols, images, icons, and other items that may be displayed or rendered, is displayed on the display 418 via the processor 402.

The electronic device 114 includes an operating system 446 and software programs, applications, or components 448 that are executed by the processor 402 and are typically stored in a persistent, updatable store such as the memory 410. Additional applications or programs may be loaded onto the electronic device 114 through the network 110, the auxiliary I/O subsystem 424, the short-range communications subsystem 432, or any other suitable subsystem 434.

A received signal is processed by the communication subsystem 404 and input to the processor 402. The processor 402 processes the received signal for output to the display 418 and/or to the auxiliary I/O subsystem 424. Data may be transmitted over the network 110. For voice communications, the overall operation of the electronic device 114 is similar. The speaker 428 outputs audible information converted from electrical signals, and the microphone 430 converts audible information into electrical signals for processing.

The input device 116 illustrated in FIG. 1 and described above is connected to the electronic device 114, by wired or wireless connection. The input device 116 receives input for controlling position and orientation of the virtual element displayed on the mixed reality headset 104. The input device 116 may be any suitable input device for the application. As indicated, the input device 116 may be any one or a combination of a haptic device such as a Touch X™ haptic device available from 3D Systems, Inc, a joystick, a vision system, an electromagnetic sensing system, an optical infrared tracker, a stereo camera system, for tracking position and orientation of another device or of a part of the user, such as the user's hands.

Figure 5:
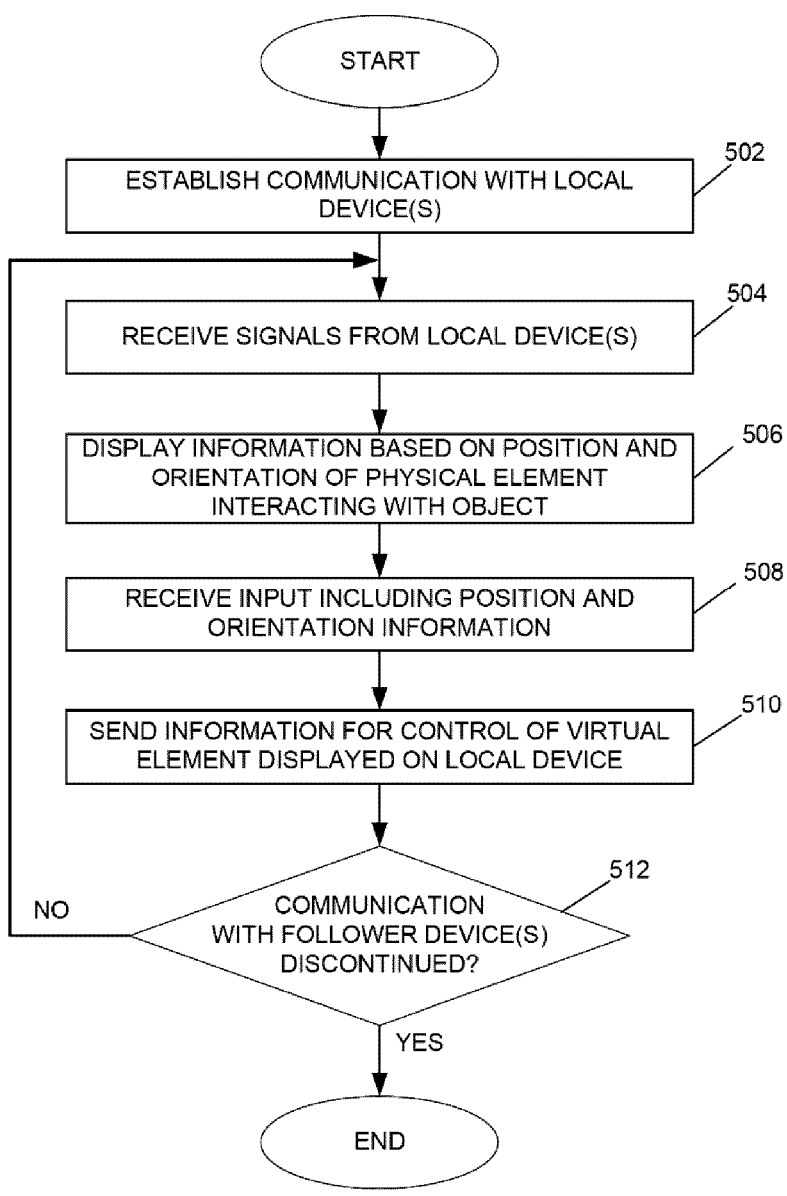
FIG. 5 is a flowchart illustrating a part of a method of interacting with an object carried out at a remote system in accordance with an aspect of an embodiment.

A flowchart illustrating a part of a method of interacting with an object carried out at a remote system 112 in accordance with an aspect of an embodiment is shown in FIG. 5. The method may be carried out by software executed, for example, by the electronic device 114. Coding of software for carrying out such a method is within the scope of a person of ordinary skill in the art given the present description. The method may contain additional or fewer processes than shown or described, and may be performed in a different order. Computer-readable code executable by at least one processor to perform the method may be stored in a computer-readable medium, such as a non-transitory computer-readable medium.

The method illustrated is carried out at the remote system 112. Communication with the local system 102 is established at 502. Thus, the electronic device 114 establishes communication with the communication device 106 and with the mixed reality headset 104 via the network 110. The network 110 may be a local area network or may include the internet. The electronic device 114 is configured to establish a secure communication link with the local system 102 with low latency of communication with the remote system, for example, of 0.5 seconds or less.

Signals are received from the local system 102 at 504. The signals received include signals received from the mixed reality headset 104 as well as signals from the communication device 106. The signals include video signals captured utilizing, for example, the external cameras 216 of the mixed reality headset 104. In addition, the signals include a map of an object at the local side. The map is generated by the mixed reality headset 104 and may be a mesh of an object or a depth map of the object or of constraints that the object is subject to. The signals received also include signals that are generated utilizing the data collection device 108. For example, the signals may include an ultrasound image generated based on signals from the data collection device 108, sensed forces, sensed temperature, images from a vision system, an electromagnetic sensing system, an optical infrared tracker, a stereo camera system, for tracking position and orientation of another device or of a part of the user, such as the user's hands.

Information is displayed at the remote system 112 at 506, based on the signals received at 604, on the display 418 of the electronic device 114. The information that is displayed includes a video feed from the video signals captured utilizing, for example, the external cameras 216 of the mixed reality headset 104.

In addition, a rendering of the map received at 504 may be displayed on the display 418 along with a representation of a physical element at a location and orientation relative to the object. For example, a virtual representation of an ultrasound probe or a virtual representation of a user's hands may be displayed along with the rendering of the map.

In the example in which the data collection device 108 is an ultrasound transducer, an ultrasound image is received at 504 and the information displayed at 506 includes the ultrasound image. The ultrasound image is dependent on the position and orientation of the ultrasound probe on the object.

Input is received at 508 via the input device 116 for remote user interaction. The input device 116 controls the position and orientation of a virtual representation of the physical element relative to the object, on the mixed reality headset. The virtual representation of the physical element may also be displayed on the display 418, relative to the rendering of the map.

In the example in which the input device 116 is a haptic device such as the Touch X™ haptic device available from 3D Systems, the map received at 504 may be utilized to constrain movement of the haptic device and for the purpose of providing force feedback to give the remote user the sensation of interaction with a physical object. The input device 116 may be utilized to detect a force applied. The map may be utilized to simulate the interaction of the physical device with the object by providing a force reaction at the input device based on an estimated mechanical impedance. The estimated impedance may be obtained from the force applied to the object by the data collection device and the consequent position change of the data collection device, or otherwise estimated using the location and force data acquired by the collection device at the local system 102. Thus, the input device 116 provides haptic feedback based on a relationship between the physical device and the map of the object.

The input device may provide additional output such as temperature, to provide a more realistic sense of interaction with the object and may provide sound.

Information is sent to the local system 102 to control the virtual representation of the physical element displayed on the mixed reality headset 104 relative to the physical object, based on the input received via the input device 116 of the remote system 112. Thus the input received via the input device 116 controls the position and orientation of the virtual representation of the physical element displayed on the mixed reality headset 104 relative to the physical object.

The input received at 508 may also include force or estimated impedance information based on a force detected at the input device 116. In addition, one or both of temperature and sound may be received and output.

The information is sent to the local system 102 at 510. The input received via the input device 116 is utilized to control the position and orientation of the virtual representation of the physical element displayed on the mixed reality headset 104. In addition, force information may also be sent to the local system 102.

The method continues while communication with the local system 102 continues. In the flowchart illustrated in FIG. 5, the process continues at 504. It will be appreciated that the process is continuous and ongoing until the communication is discontinued at 512.

Figure 6:
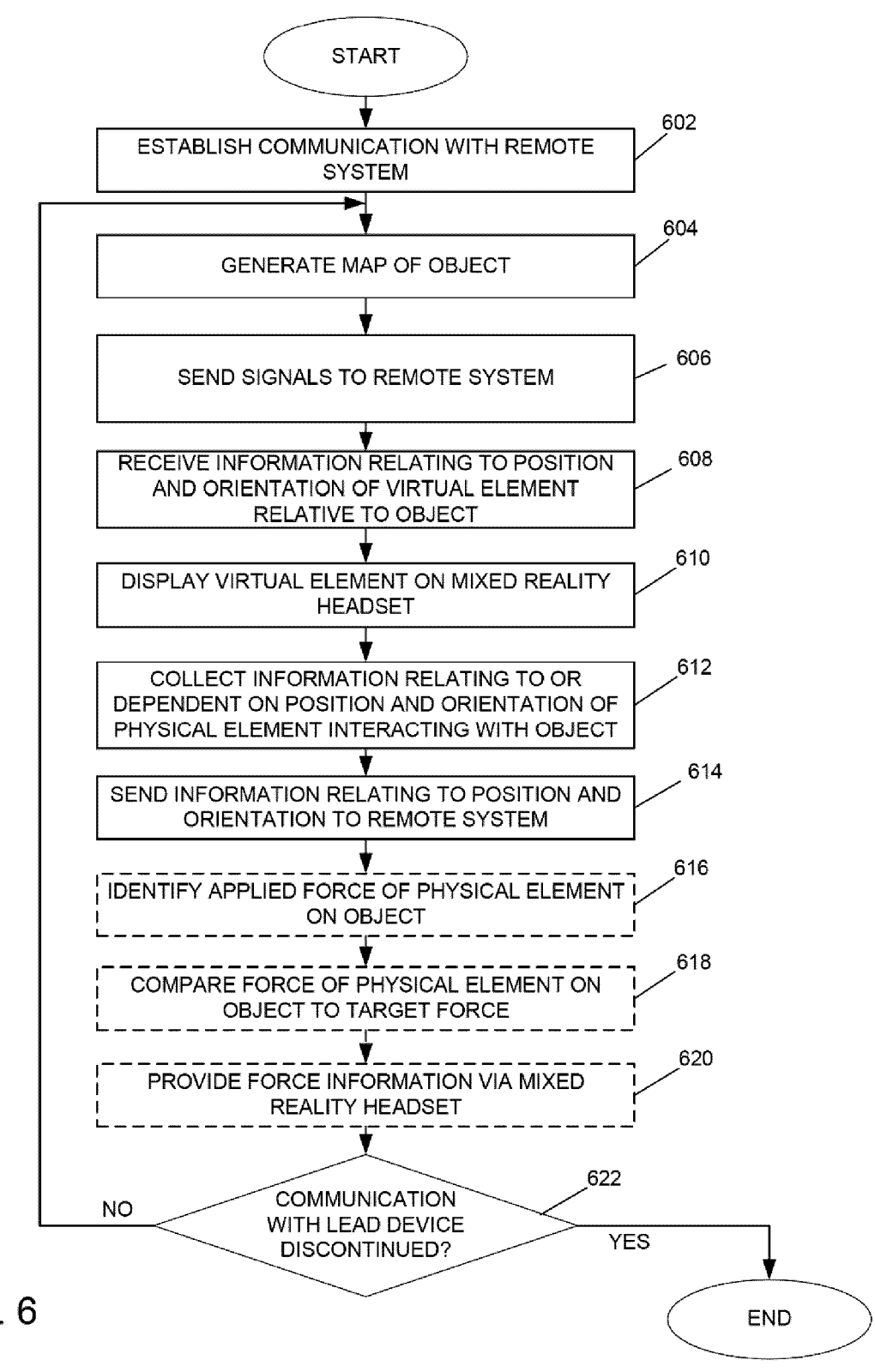
FIG. 6 is a flowchart illustrating a part of a method of interacting with an object carried out at a local system in accordance with an aspect of an embodiment.

A flowchart illustrating another part of a method of interacting with an object carried out at a local system 102 in accordance with an aspect of an embodiment is shown in FIG. 6. The method may be carried out by software executed, for example, by the mixed reality headset 104 and the communication device 106. Coding of software for carrying out such a method is within the scope of a person of ordinary skill in the art given the present description. The method may contain additional or fewer processes than shown or described, and may be performed in a different order. Computer-readable code executable by at least one processor to perform the method may be stored in a computer-readable medium, such as a non-transitory computer-readable medium.

The method illustrated is carried out at the local system 102. Communication with the remote system 112 is established at 602. Thus, the communication device 106 and the mixed reality headset 104 establish communication with the electronic device 114 via the network 110. As indicated above with reference to FIG. 5, the network 110 may be a local area network or may include the internet. The communication device 106 and the mixed reality headset 104 are configured to establish a secure communication link with the electronic device 114 with low latency of communication with the remote system, for example, of 0.5 seconds or less.

The mixed reality headset 104 generates a map of an object at 604. The map may be a mesh of an object or a depth map of the object or of constraints that the object is subject to. For example, mesh may be measured by the mixed reality headset 104 as a set of points in the space, represented in a coordinate frame in which the mixed reality headset 104 is located and utilized. While the mixed reality headset captures a spatial mesh of the environment of the local system 102, a smaller region may be identified by bounds around the object to identify the region in which the object is located.

Signals are sent from the local system 102 to the remote system 112 at 606. The signals include signals sent by the mixed reality headset 104 as well as signals from the communication device 106. The signals include video signals captured utilizing, for example, the external cameras 216 of the mixed reality headset 104. In addition, The signals that are sent at 606 include the map of the smaller region in which the object is located, and that is generated by the mixed reality headset 104.

Information is also received at the local system 102 at 608. The information received at 608 is information for controlling a virtual representation of the physical element displayed on the mixed reality headset 104 relative to the physical object. The information received is based on the input received via the input device 116 of the remote system 112.

The virtual representation of the physical element is displayed on the mixed reality headset at 610. The virtual representation may be, for example, a virtual representation of an ultrasound probe, a virtual representation of a hand or a pair of hands, or any other virtual representation. The input received via the input device 116 at the remote system 112, controls the position and orientation of the virtual representation of the physical element displayed on the mixed reality headset 104 relative to the physical object.

The data collection device 108, is utilized to collect information relating to or dependent on the position and orientation of a physical element interacting with the object at 612. The data collection device 108 may be part of or housed in the physical element that interacts with the object and obtains the information. In one example, the data collection device 108 is an ultrasound transducer that is housed in the ultrasound probe that interacts with the object and collects the information in the form of ultrasound signals that are utilized to generate an ultrasound image. Alternatively, the data collection device 108 may be separate of the physical element that interacts with the object. For example, the data collection device 108 may be a vision system for identifying and tracking a position and orientation of a physical element that interacts with the object. In this example, the physical element may be a hand or hands of a local user interacting with the object.

The information relating to or dependent on position is sent, by the communication device 106 to the remote system 112 at 614. In the example in which the data collection device 108 is an ultrasound transducer, the information includes the ultrasound image generated from the ultrasound signals. In the example of the vision system, the position and orientation of the physical device, which may be the hands of the local user, are sent to the remote system 112. In the example of a temperature sensing system, the information includes a temperature map.

Optionally, the force applied by the physical element on the object may be identified or detected at 616. The force may be detected utilizing any suitable force detection arrangement. For example, one or more force sensors may be coupled to the data collection device to determine force applied. Optionally, force may be determined based on the deflection of the object with which the physical element interacts.

The applied force may be compared at 618 to a target applied force, which may be based on the applied force at the input device 116 of the remote system 112, or may be a stored target applied force, for example. The map generated at 604 may be utilized to provide a virtual surface with mechanical impedance during use of the input device to simulate the interaction of the physical device with the object by providing a force reaction which becomes the target applied force.

Force information is displayed on the mixed reality headset 104 at 620, based on the comparison of the applied force to the target applied force. An attribute of the virtual representation of the physical device may be varied based on the comparison to provide an indication of whether the force is too great, too little, or is acceptable. For example, the color of the virtual representation may be varied. Alternatively, an error bar may be displayed on the virtual representation, an arrow may be displayed on or near the virtual representation, or a second virtual representation may be displayed that is offset by an amount and in a direction that is dependent on the comparison.

Optionally, the virtual representation of the physical device may be located relative to the object based on a comparison of mechanical impedance. For example, the virtual representation may be located at a greater depth or less depth into the object to illustrate that greater or less force is required to match the desired force at the input device 116 of the remote system 112. The degree of offset may be proportional to the estimated impedance, or may be dynamically controlled without explicitly estimating impedance such that when the desired force is matched, the offset of the virtual representation into the object is the same as the depth of the physical device into the object; i.e., there is no offset.

The method continues while communication with the remote system 112 continues. In the flowchart illustrated in FIG. 6, the process continues at 604. It will be appreciated that the process is continuous and ongoing until the communication is discontinued at 622.

Advantageously, the local system may be, for example, located in an ambulance, a first response vehicle, a remote health care clinic, or even a private house where a patient is located and where an expert sonographer is not available. The remote system may be located at a hospital, medical clinic, or office where an expert is located remote from the patient.

Figure 7:
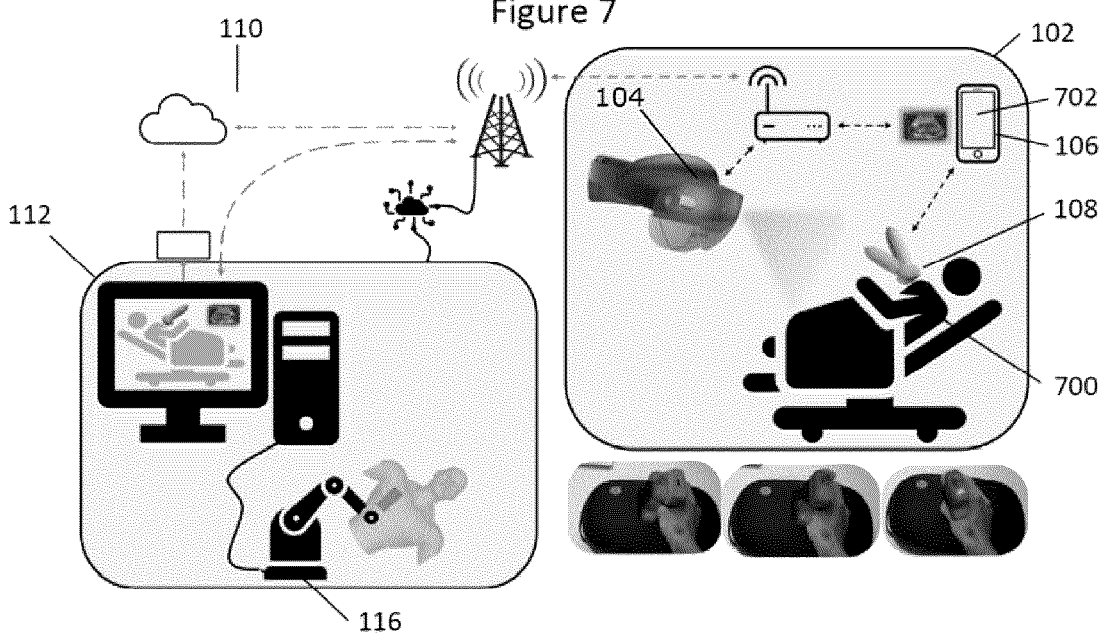
FIG. 7 is a block diagram of one example of an apparatus for remote interaction including a local system and a remote system in accordance with an aspect of an embodiment.

Reference is now made to FIG. 7, which illustrates a particular example of an implementation of an apparatus for remote interaction including a local system and a remote system in accordance with an aspect of an embodiment. In the present example, the method and apparatus is utilized to carry out an ultrasound procedure on a patient and is referred to herein as a human teleoperation or teleultrasound.

The local system 102 includes the mixed reality headset 104, which in this example is a Hololens 2™ available from Microsoft™. The local system 102 also includes the communication device 106, which in this example is a smartphone that includes a display 702. The communication device 106 is connected to the data collection device 108, which is an ultrasound transducer that is part of the ultrasound probe for use on the patient 700. An example of an ultrasound probe for this embodiment is a C3 HD₃ handheld wireless ultrasound device available from Clarius™, Vancouver, BC.

Ultrasound image data that is dependent on the position and orientation of the ultrasound probe on the patient, is collected by the ultrasound transducer and provided to the communication device 106. The mixed reality headset 104 includes the external cameras as described above, which provide a visual image of the ultrasound probe on the patient and the visual image is sent to the remote system 112.

The remote system 112 includes a desktop computer which in this example is the electronic device 114. The desktop computer includes a display 704 for displaying information.

In this example, the input device 116 is connected to the desktop computer by wired connection. The input device 116 is a Touch X™ haptic device available from 3D Systems, Inc.

In use, the mixed reality headset 104 is worn by the local system user and is utilized to display a virtual ultrasound probe projected into the environment viewed by the local system user.

The user of the remote system remotely controls this virtual ultrasound probe to move the virtual ultrasound probe into the desired position and orientation and utilizing the desired force.

The local system user utilizes the physical ultrasound probe to follow the position and orientation of the virtual ultrasound probe projected utilizing the mixed reality headset.

Live ultrasound images are transmitted wirelessly from the data collection device 108, which is the ultrasound transducer to the communication device 106 of the local system 102 and to the electronic device 114 of the remote system 112.

The mixed reality headset 104 also captures a mixed reality video of the scene with the mixed reality overlays in position, also referred to as a mixed reality capture, and shares the mixed reality video live with the user of the remote system 112 via a WebRTC interface for positional feedback. The high quality ultrasound images are displayed on the display 704 in real time, along with video of the patient with the virtual ultrasound probe and physical ultrasound probe shown. In addition, the user of the remote system 112 is in verbal communication with the user of the local system.

Additionally, a spatial mesh of the patient, generated automatically by the mixed reality headset 104, is sent to the remote system 112 on demand. The mesh is rendered haptically as a virtual fixture for the input device 116 to provide the sensation that the remote user is physically touching and interacting with the patient 700.

The mesh is shown on the display 704 of the electronic device 114 along with the virtual ultrasound probe for further position and orientation feedback. Thus, the virtual ultrasound probe is located in position and orientation relative to the patient 704. The mesh may include properties that enable the realistic rendering of the object. For example, the mesh may be endowed with one or more of colour, texture, mechanical impedance from local measurements, and temperature properties.

The input device 116 is utilized to naturally and intuitively control position and orientation. Additional coarse/rough positioning may be controlled utilizing, for example, arrow keys on a keyboard of the electronic device 114, a joystick or a computer mouse, or by a pinch and drag by the local system user wearing the mixed reality headset 104.

When the local system 102 is utilized to change the probe position, input from the input device 116 is ignored to avoid conflicting position and orientation commands.

The input device 116 is also utilized to input a desired force. Force information from the input device 116 is sent to the local system 102 and displayed on the mixed reality headset 104 by comparing the force input utilizing the input device 116 to force input utilizing force sensors on the physical ultrasound probe and varying the length and color of an error bar on the virtual ultrasound probe displayed on the mixed reality headset 104.

Force information is provided on the mixed reality headset without distracting from the position and orientation of the virtual ultrasound probe.

The ultrasound images, mixed reality capture, and patient mesh shown with the virtual ultrasound probe in position and orientation, are displayed on the display 704 of the electronic device 114 of the remote system 112.

Optionally, a virtual reality headset may also be used with the remote system 112 to further increase the immersive and realistic experience provided to the remote system user.

Figure 8:
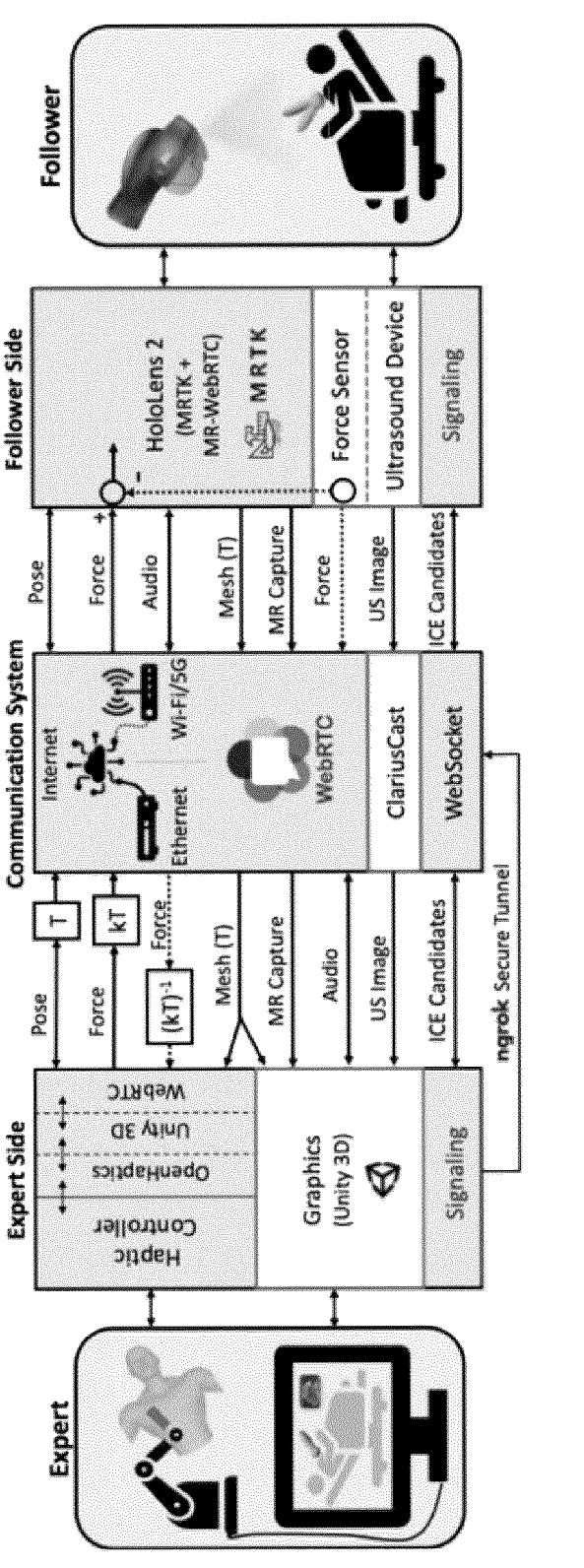
FIG. 8 illustrates an example of a communication architecture for the apparatus for remote interaction including the local system and the remote system.

Reference is made to FIG. 8 which illustrates an example of communication architecture for the apparatus for remote interaction including the local system, referred to herein as the follower side, which is operated by a follower, and the remote system, referred to herein as the expert side, which is operated by an expert, i.e., a sonographer.

Data speeds of 1 Mbps or greater are utilized for high quality transmission of ultrasound images. In addition, an audio/video conferencing system is utilized. High rate of transmission of the ultrasound probe pose and force are also desired. A spatial mesh of the patient generated by the mixed reality headset 104 is sent as well. The bandwidth accounting, utilizing rough approximations of bandwidth, is shown in Table 1. Based on these approximations, the data that is communicated may total 10 Mbps.

TABLE 1

| Bandwidth for Apparatus | | | |
|---|---|---|---|
| Data | Size | Rate | Bandwidth |
| Force/Torque | 48 bits | 100 Hz | 4.8 kbps |
| Position | 48 bits | 100 Hz | 4.8 kbps |
| Orientation | 64 bits | 100 Hz | 6.4 kbps |
| Video | — | 30 Hz | 4 Mbps |
| Audio | — | — | 96 kbps |
| Ultrasound | — | — | 3 Mbps |

The mixed reality headset 104 provides the main interface for the local system user through a Unity application built utilizing the Microsoft Mixed Reality Toolkit (MRTK). The desired position and orientation as well as force are received from the remote system 112 and the actual force, position, and orientation are determined by the local system 102. The patient mesh as well as MR captures of the scene are sent from the local system 112 to the remote system 112. All communication between the electronic device 106 and the mixed reality headset 104 is achieved via a WebRTC architecture using Microsoft's Mixed Reality WebRTC API.

To establish a WebRTC connection between the remote system 112 and the local system 102, a signaling server written in Python™ is used to facilitate the Interactive Connectivity Establishment (ICE) protocol during which session description protocol (SDP) messages are exchanged, and a handshake is completed. To obtain the SDPs, a session traversal using NAT (STUN) server hosted by Google™ is utilized. The ICE messages are encrypted for security, and the signaling server is password protected.

The user interfaces of the remote system 112 and the local system 102 were built utilizing Unity™ From Unity Technologies, Inc. using C #. The user interfaces of the remote system 112 and the local system 102 communicate via WebRTC using Mixed Reality WebRTC API from Microsoft™. The mixed reality headset 104 runs a different build of the library which is compatible with the Universal Windows Platform (UWP) architecture and ARM64 CPU of the mixed reality headset 104.

To reduce latency, the orientation of the virtual ultrasound probe is encoded as a quaternion. The mesh is also preprocessed to decrease the data utilized to transfer the mesh to the remote system 112.

The remote system Unity application utilizes OpenHaptics software development toolkit (SDK) to drive the haptic input device and the haptic interactions, as well as OpenVR SDK to provide an optional immersive view on an Oculus Rift DK2 virtual reality headset.

The MR capture is displayed on the display 704 of the electronic device 114, utilizing the Unity application. The patient mesh and virtual ultrasound probe are also displayed utilizing the Unity application. The live ultrasound images are displayed separately on the display 704 of the electronic device 114.

The use of the Unity application provides multiple channels of information that may be utilized to make clinical and diagnostic decisions. Clarius Cast API by Clarius™ facilitates real time streaming of the ultrasound images from the physical ultrasound probe to the communication device 106. The audio/video call utilizes the microphone and external cameras of the mixed reality headset to stream the MR capture.

The control of position and force, as well as force feedback to the remote system user is provided by the haptic input device, which as indicated is a Touch X™ haptic device available from 3D Systems, Inc. The Touch X™ haptic device is a 6 degree of freedom serial arm with three actuated arm joints that provide haptic feedback, three passive spherical wrist joints, and a stylus-like end effector with two buttons. A 3D-printed shell in the shape of the C3 $HD_3$ is attached to the stylus for the remote user to grasp.

The remote user may determine whether greater or less force is to be applied based on the quality of the ultrasound image, the video feed of the patient, and verbal communication with the local system user. The desired force may be indicated through the input device 116.

The Touch X™ haptic device utilized in this example is configured to apply forces precisely but is limited to 7.9 N. Thus, ultrasonographers can directly input their desired force by applying up to 7.9 N of force. While ultrasound procedures ordinarily involve forces in the 0 to 20 N range, the force input can be scaled before being compared to the local user's applied force. Ultrasonographers routinely suffer from musculoskeletal injuries due to the repeated loading over their careers, so reducing their required input force may be beneficial.

On the mixed reality headset 104, the colour of the virtual ultrasound probe may be varied to indicate "more force", "less force", or "good force", based on the input from the two buttons at the input device 116. The colour may be varied, for example, by changing the colour to red to indicate "more force", blue to indicate "less force", and green to indicate "good force", and interpolating linearly in between these colors for "slightly more force", and so on.

Utilizing the colour change, the local user may focus on following the position and orientation and there is no need to look elsewhere to determine the desired force.

EXAMPLES

The local system is referred to herein as the follower side, which is operated by a follower, and the remote system is referred to herein as the expert side, which is operated by an expert, i.e., a sonographer.

Mesh Management

The mesh data was preprocessed at the mixed reality headset 104 and sent via WebRTC. The mixed reality headset 104 repeatedly captured a spatial mesh of the environment in the viewframe of the external cameras.

Only the patient's mesh was utilized at the remote system 112, however. A bounding box around the patient was defined, delineating which subset of mesh vertices constituted the patient mesh to be extracted.

To define the bounding box, the mixed reality headset 104 displayed three spherical markers when the application was executed. The markers were pinched and dragged into position at three corners of the bed of the patient. The fourth corner was calculated automatically by identifying the rectangle with the lowest sum of the squared displacements to make the other three markers coincident with its corners, and placing the final marker at the fourth corner.

A semi-transparent plane spanning the rectangle was displayed and dragged to set the height of the bounding box to remove mesh points from above including from the ceiling. The markers and plane were hidden after selection of a "Finished" button utilizing the mixed reality headset 104. Although not shown, a button on the control menus was provided to recall the markers and plane to edit the bounding box.

The local system user pressed the "Send Mesh" button on a menu using the mixed reality headset 104, and an option to scan the patient was provided to ensure quality of the mesh. During the scan, the mesh edges were displayed on the mixed reality headset 104, projecting the edges onto the real world to provide an indication of quality and which areas may be improved by scanning over them. Each vertex of the mesh was then iterated through to check that the vertex was within the bounding box. To do so, the vertex point was first projected into the plane of the defined rectangle. Each edge of the rectangle represented a half-space partition atx≤ bi, such that in total the rectangle was a convex set of points defined by the intersection of the four half-spaces. By placing the four a; vectors as the rows of a matrix, A, a mesh point's inclusion in the rectangle was determined by checking if Ax≤ b (component-wise) and the vertical component was less than the bounding box height. This calculation has a very low computational cost on the mixed reality headset 104.

Any mesh triangles with only one vertex left were ignored, while mesh triangles with two vertices in the bounding box were completed by projecting the third vertex onto the boundary of the bounding box. This smoothed the edges of the cropped patient mesh, which was then expressed as a list of vertex points (3-vectors) and a list of indices defining which points formed triangles together. These lists were sent via ROS as a simple message containing float and int arrays, and were converted back to a Unity mesh on the remote system 112 by the electronic device 114.

Pose Registration

The spatial mesh of the patient was used as a virtual fixture for the haptic input device to interact with. In addition, the mesh provided visual feedback for the local system user for positioning of the physical ultrasound probe, and facilitated the position and orientation registration between the virtual ultrasound probe displayed on the display 704 of the electronic device 114, and the virtual probe displayed using the mixed reality headset 104, and the patient 700.

In the following, $T_{ij} \in SE(3)$ is the 4×4 homogeneous transformation matrix transforming frame i to frame j. The patient mesh was measured by the mixed reality headset 104 as a set of points in space, {xi} represented in the coordinate frame of the local environment of the mixed reality headset 104. When the mesh is sent, it is placed in the expert's scene in the centre of the screen, at a comfortable scale. It is oriented such that the expert's x-axis (left-right on the expert's monitor) aligns with the major axis of the patient, so that the expert observes the patient from the side on, and the vertical axis is kept constant. This sequence uniquely defines a transformation, $T_{hc}$, that transforms from the mixed reality headset head frame to the expert's Unity camera frame. The camera pose in Unity, $T_{1c}$, is known. The mixed reality headset, which in this example is the Hololens 2™, provides accurate SLAM through its spatial awareness interface, so the transform from the mixed reality headset base frame to the head frame, $T_{0h}$, is also known.

The virtual ultrasound probe is roughly positioned by the follower relative to the patient, as explained before. This sets the pose of the probe on the follower side, in the mixed reality headset base coordinate frame: Top. Thus, a chain of transformations is defined to determine the virtual probe pose in the expert scene:

$$T_{1p} = [T_{1c} T_{hc} T_{0h}^{-1}] T_{0p} \tag{1}$$

Thus the registration was achieved, providing the transform T shown in FIG. 8. The coordinate transforms are illustrated in FIG. 9.

Data Latency

To determine the latency of the WebRTC system, a separate data channel was created on which timestamps were sent from follower to expert and back. Each time a message was received or sent, a timestamp was appended to the message, for a total of four timestamps, T1, T2, T3, and T4. Here, T1 and T4 are measured at the follower, who initiates the chain, and T2 and T3 are measured at the expert side. The round-trip time is then simply (T2-T1)+(T4-T3). This method accounts for drift in the clock time between the expert and follower devices, which can be larger than the expected latency of the communication itself. The clock drift is given by (1/2)[(T2-T1)-(T4-T3)]. Isolated measurements of latency will produce overly optimistic results since none of the bandwidth is used by the communication of the actual data. For more realistic network conditions, the measurements were carried out while the full system was running. The communication of timestamps required negligible additional bandwidth as the packets were sent in bursts of 10, once per second. The resultant latency histograms are shown in FIG. 10A and FIG. 10B.

Latency for video conferencing was determined by making sharp sound that was picked up by the microphone of the mixed reality headset 104, transmitted to the electronic device 114 of the remote system 112 and replayed. A microphone recorded both sounds, and the delay time was determined in MATLAB™. This test was repeated 20 times, with little variance. These results are summarized in Table 2.

TABLE 2

| Latency of Communication System | |
| --- | --- |
| Network Type | Mean Latency (Round Trip Time/2) |
| Local WiFi | 2.3 ms |
| Separate WiFi | 3.3 ms |
| 5G (strong signal) | 15.8 ms |
| 5G (medium signal) | 17.6 ms |

The latencies over WiFi are extremely fast, while the 5G latencies too are sufficiently small to implement most control systems without risking instability or decreased performance.

Overall Latency and Precision

The total latency also included the reaction times of the local system user in following the position and orientation of the virtual ultrasound probe displayed utilizing the mixed reality headset 104.

To test the resulting latency of the system as a whole, as well as the precision, two series of random motions were recorded using the haptic controller. Trial 1 included smooth, continuous motions while trial 2 included sharp motions followed by holding the pose for a few seconds. The second trial was similar to a sequence of step response tests. Both series were carried out for about 150 seconds.

An end effector, similar in size and shape to the shell of the physical ultrasound probe was mounted to the end of the input device 114 for grasping by the local system user.

Each series was played back on the mixed reality headset 104 while the local system user followed the virtual ultrasound probe position and orientation with the physical ultrasound probe mounted on a haptic controller. In this way, the physical ultrasound probe position and orientation was also recorded for comparison of the position and orientation of the virtual ultrasound probe controlled by the input device 114, to that of the physical ultrasound probe.

Precision

Figure 11:
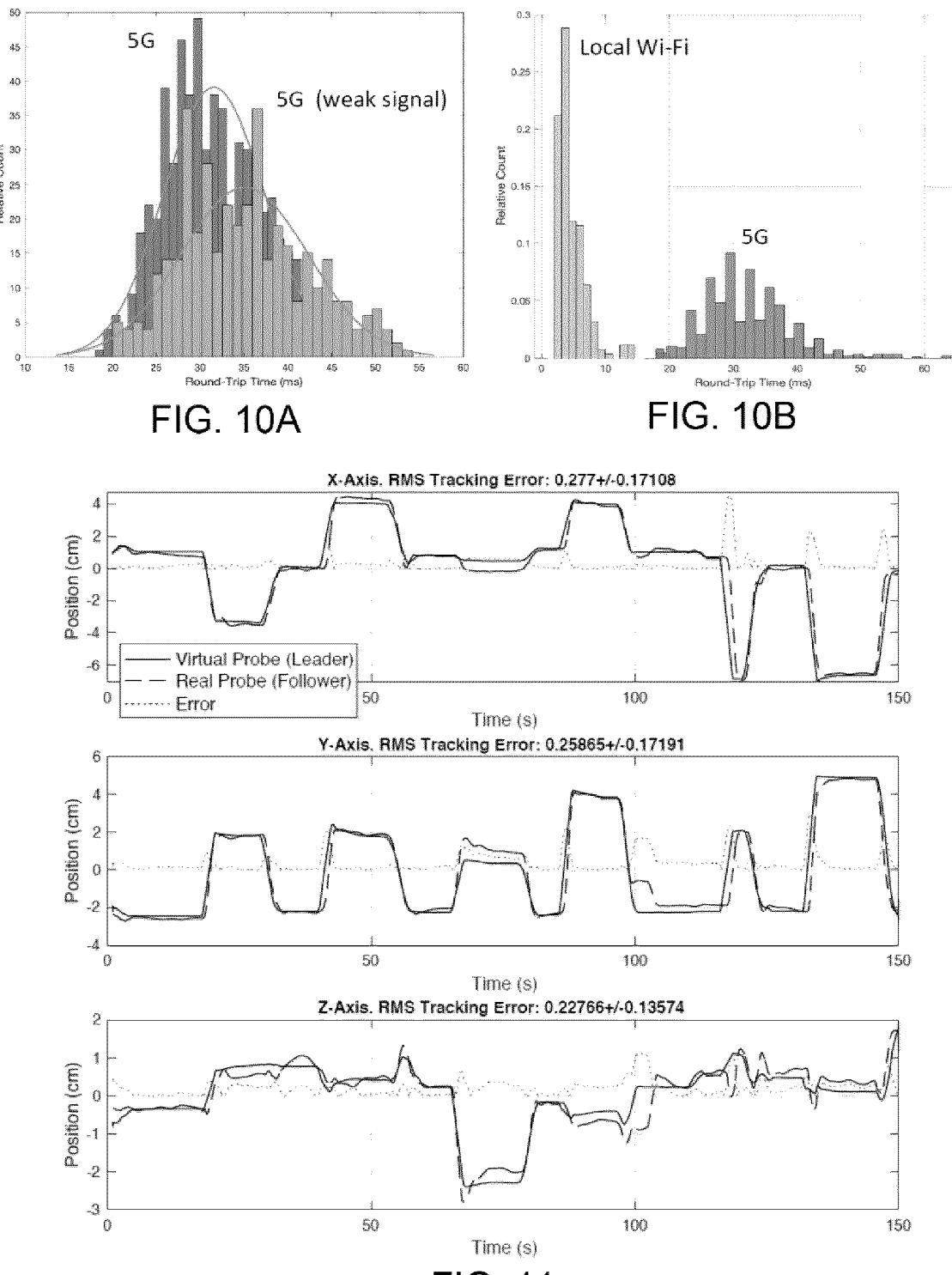
FIG. 11 shows results of a comparison of position of a physical ultrasound transducer of the local system to the input device of the remote system in the X, Y, and Z axes, respectively.

The precision was studied separately for the position and orientation of the physical ultrasound probe. For position, each axis was compared individually and an error signal was obtained by subtracting the virtual ultrasound probe and physical ultrasound probe position elements. The signals for the series of sharp motions are shown in FIG. 11.

The root mean square (RMS) positional error of each axis and the resulting Euclidean displacement for both trials are shown in Table 3. Both trials showed very similar positional results despite the different motions. Both average values were slightly inflated because they included the initial large position error. The sharper motions in trial 2 were likely the reason why the mean offset in that trial was larger. The mean error was 36% of the width of the ultrasound probe head, which was 2 cm.

TABLE 3

| RMS Tracking Error and Resulting Euclidean Displacement | | | | |
|---|---|---|---|---|
| Axis | X | Y | Z | Eucl. |
| Trial 1 Error (mm) | 4.6 | 3.1 | 3.7 | 6.7 |
| Trial 2 Error (mm) | 3.7 | 6.0 | 2.9 | 7.6 |

Figure 12:
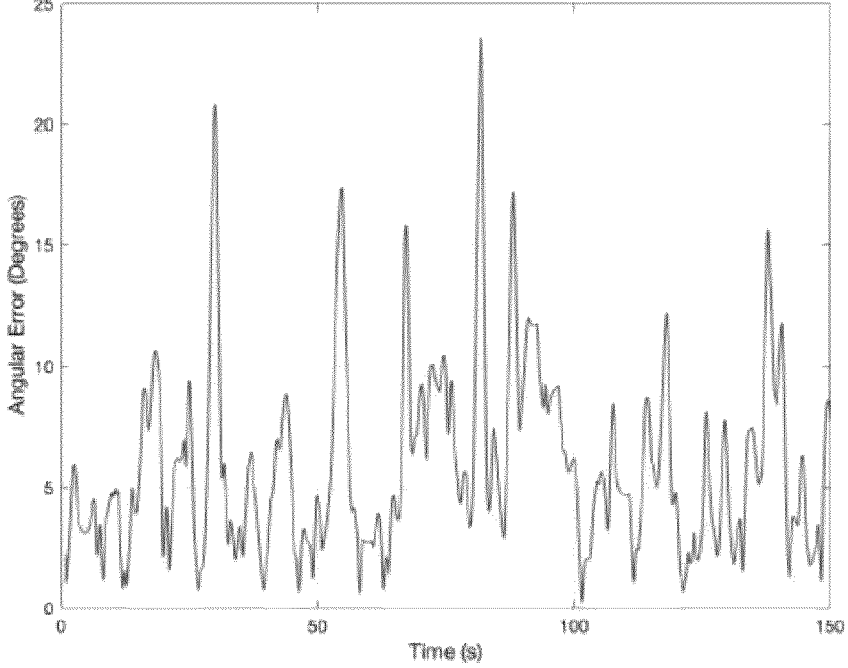
FIG. 12 shows angular displacement between position of a physical ultrasound transducer of the local system and the input device of the remote system.

To quantify the orientation error, the rotation quaternion from virtual ultrasound probe controlled by the input device 114, to the physical ultrasound probe was calculated at every sampling time and converted to an axis-angle representation to find the error as a single angular displacement value in degrees. The angular displacement between the virtual ultrasound probe controlled by the input device 114 and the physical ultrasound probe is shown in FIG. 12 for trial 1.

The mean angular displacements between virtual ultrasound probe controlled by the input device 114 and the physical ultrasound probe were 5.87° and 6.89° for trial 1 and trial 2 respectively. Ignoring the high peaks above 12° where the orientation was suddenly changed more dramatically and the local system user had not yet reacted, the errors are reduced to 5.2° and 5.5° respectively, which represent steady-state errors. The mean non-steady-state error in trial 2 was larger because the motions were sharper.

In summary, the mean tracking error was measured to be 7.1+0.3 mm and 6.3+0.5° for the general process and smaller when smoother, slower motions are utilized, as is typical in ultrasonography. Mean steady-state error was found to be 4.4+2.8 mm and 5.4+2.8°.

Latency

Using the same measurements for determining precision, the average latency was determined by determining the time delay between the position signals from the virtual ultrasound probe controlled by the input device 114 and the position signals from the physical ultrasound probe.

In particular, a varying time delay was applied to the recorded position signal of the virtual ultrasound probe controlled by the input device 114. The resulting normalized cross-correlation between the recorded position signals of the physical and virtual ultrasound probes was maximized as a function of time delay. By shifting the virtual ultrasound probe position signal in time until it most closely matched the real ultrasound probe, the approximate lag of the local user in tracking the remote user's commands could be determined.

The approximate latencies in the three positional axes are shown in Table 4. On average, the total latency from both the communication system and response time at the physical ultrasound probe was 0.27 seconds.

TABLE 4

| Mean Teleoperation Latencies | | | | |
|---|---|---|---|---|
| | X | Y | Z | Mean |
| Trial 1 Latency (sec) | 0.34 | 0.27 | 0.31 | 0.31 |
| Trial 2 Latency (sec) | 0.40 | 0.30 | 0.01 | 0.24 |

Procedure Efficiency

The above-described tests establish the efficacy of the apparatus and architecture in general. To verify that the apparatus and architecture were suitable for remote interaction with an patient, two different procedures were carried out on two healthy volunteers for each of the two procedures. For each volunteer, the procedure was carried out first directly by an expert sonographer, second by an inexperienced person guided only verbally by the expert, and finally utilizing the present teleoperation system in which a different inexperienced person acted as the local system user and was guided by an expert as the remote system user.

The first test carried out directly by an expert sonographer established the true measured values and the time taken to complete the procedure for comparison purposes. The second and third tests provided a comparison between currently commercially available tele-guidance systems and the apparatus and method of the present application.

The two procedures involved specific, quantitative endpoints to facilitate quantifying the effectiveness of the method by comparison of the measured values, and the time taken to complete the procedure. The procedures were (1) measurement of the kidney size (craniocaudal and transverse dimensions) of the patient and (2) measurement of the inferior vena cava diameter in the infrarenal segment.

Each inexperienced person was guided verbally by the expert for one procedure and operated the local system guided by an expert as the remote user utilizing the present apparatus for remote interaction for the other procedure. This testing method was utilized to reduce learning of the procedure thus introducing bias into the test.

Procedure times and values differed between the patients due to differences in anatomy. However, these differences should cancel out when studying the percent changes in the metrics between tests on a given patient. Additionally, though one inexperienced person may be a faster learner than another, each inexperienced person participated in one test of each of the verbal guidance and the teleoperation methods to reduce the chance that bias was introduced. The results are outlined in Table 5 and show a clear improvement in both speed and precision utilizing the present teleoperation method compared to a verbal guidance method.

TABLE 5

| | Patient | Control | | Verbal | | Teleoperation | |
|---|---|---|---|---|---|---|---|
| | | | | Testing Results Utilizing 4 Subjects | | | |
| Procedure | # | Time | Value | Time | Value | Time | Value |
| Kidney | 1 | 1:13 | 113 × 49 mm | 7:01 | 110 × 59 mm | 1:20 | 111 × 54 mm |
| Kidney | 2 | 1:43 | 118 × 50 mm | 1:25 | 123 × 46.5 mm | 1:52 | 112 × 46.9 mm |
| Vena Cava | 3 | 0:45 | 18.2 mm | 4:20 | 17.3 mm | 0:50 | 16.8 mm |
| Vena Cava | 4 | 0:39 | 17.4 mm | 3:30 | 21 mm | 0:47 | 15.9 mm |
| Averages | | Time | Error | Time | Error | Time | Error |
| Kidney | | 1:28 ± 0:21 | 0.0 mm | 4:13 ± 3:58 | 4 × 12 mm | 1:36 ± 0:23 | 4 × 4 mm |
| Vena Cava | | 0:42 + 0:04 | 0.0 mm | 3:55 + 0:25 | 2.3 mm | 0:49 + 0:02 | 1.5 mm |

CONCLUSION

Based on the testing carried out, the teleoperation error even in free space, unconstrained by the surface of a patient, was small at approximately 7.1+4.4 mm and 6.4+4.0°. The steady-state error was 4.4+2.8 mm and 5.4+2.8°. While a human hand supported at the forearm may achieve accuracy up to 0.34 #0:16 mm, an unsupported arm on a slippery surface such as in an ultrasound application has much lower accuracy. Thus, the precision of the present apparatus and method was approximately on the same order of magnitude as that of the human hand itself. A latency of about 0.5 seconds or less is desirable. In the experiments carried out, the latency was about 0.27 seconds on average.

The apparatus and method of remote interaction described herein may be utilized for more than the ultrasound teleoperation. For example, the apparatus and method may be utilized for remote maintenance or manufacturing using other tools or devices for data collection at the local system.

In addition, the remote system user, also referred to as the expert, may choose any of a library of different virtual tools on demand, thus guiding not only the exact motion and force, but also which tool is utilized. Further communication channels may be added to the system, for example, by creating a new channel in the WebRTC connection. Thus, additional or other sensors and devices may be integrated depending on the application.

The described embodiments are to be considered as illustrative and not restrictive. The scope of the claims should not be limited by the preferred embodiments set forth in the examples, but should be given the broadest interpretation consistent with the description as a whole. All changes that come with meaning and range of equivalency of the claims are to be embraced within their scope.

The invention claimed is:

1. An apparatus for remote interaction with an object, the apparatus comprising:
    a local system comprising:
        a mixed reality headset configured to display a virtual representation of a physical element relative to the object; and
        a device configured to obtain information relating to or dependent on position and orientation of the physical element interacting with the object;
    a remote system located remote from the object and in communication with the local system, the remote system including:
        an electronic device including a display for displaying an image based on the information relating to or dependent on the position and orientation of the physical element interacting with the object; and
        an input device for remote user interaction and configured to control position and orientation of the virtual representation displayed on the mixed reality headset, wherein the input device is a 6 degree of freedom input device utilized to control the position and orientation of the virtual representation;
    wherein the remote system is configured to communicate with the local system with latency of 0.5 seconds or less, facilitating alignment of the physical element with the position and orientation of the virtual representation,
    wherein the local system generates a map of the object, and the input device provides haptic feedback based on one or both of a relationship between the physical element and the object, and a relationship between the virtual element and the map of the object, and,
    wherein the map comprises a mesh or a depth map of constraints that the object is subject to.

2. The apparatus of claim 1, wherein the local system includes a force detection arrangement configured to detect a local applied force by the physical element interacting with the object.

3. An apparatus for remote interaction with an object, the apparatus comprising:
    a local system comprising:
        a mixed reality headset configured to display a virtual representation of a physical element relative to the object; and
        a device configured to obtain information relating to or dependent on position and orientation of the physical element interacting with the object;
    a remote system located remote from the object and in communication with the local system, the remote system including:
        an electronic device including a display for displaying an image based on the information relating to or dependent on the position and orientation of the physical element interacting with the object; and
        an input device for remote user interaction and configured to control position and orientation of the virtual representation displayed on the mixed reality headset, wherein the input device is a 6 degree of freedom input device utilized to control the position and orientation of the virtual representation;
    wherein the remote system is configured to communicate with the local system with latency of 0.5 seconds or less, facilitating alignment of the physical element with the position and orientation of the virtual representation wherein the local system includes a force detection arrangement configured to detect a local applied force by the physical element interacting with the object, wherein the input device comprises a haptic input device configured to determine remote applied force, and wherein the local system is configured to compare the local applied force to the remote applied force and the local system is configured to provide comparison information.

4. The apparatus of claim 3, wherein the mixed reality headset is configured to vary an attribute of or associated with the virtual representation based on the comparison information.

5. The apparatus of claim 3, wherein the mixed reality headset is configured to offset the virtual representation by an amount and in a direction based on an impedance value of the object, estimated using the local applied force and position of the physical element relative to the object.

6. The apparatus of claim 3, wherein the device configured to obtain information relating to or dependent on position and orientation comprises an imaging device configured to obtain an image of the physical element interacting with the object.

7. The apparatus of claim 3, wherein the device configured to obtain information relating to or dependent on position and orientation comprises a transducer.

8. An apparatus for remote interaction with an object, the apparatus comprising:

a local system comprising:

a mixed reality headset configured to display a virtual representation of a physical element relative to the object; and a device configured to obtain information relating to or dependent on position and orientation of the physical element interacting with the object;

a remote system located remote from the object and in communication with the local system, the remote system including:

an electronic device including a display for displaying an image based on the information relating to or dependent on the position and orientation of the physical element interacting with the object; and an input device for remote user interaction and configured to control position and orientation of the virtual representation displayed on the mixed reality headset, wherein the input device is a 6 degree of freedom input device utilized to control the position and orientation of the virtual representation;

wherein the remote system is configured to communicate with the local system with latency of 0.5 seconds or less, facilitating alignment of the physical element with the position and orientation of the virtual representation, wherein the input device comprises a three dimensional haptic controller for controlling the position and orientation of the virtual representation and providing haptic feedback to the remote user.

9. The apparatus of claim 8, wherein the mixed reality headset is configured to provide a three dimensional mesh of the object and, wherein the three dimensional haptic controller utilizes the mesh as a virtual fixture that has an impedance equal to an estimated object impedance value.

10. A method of interaction with an object comprising:

establishing communication between a local system and a remote system located remote from the object;

displaying on a mixed reality headset of the local system, a virtual rendering of a physical element positioned and oriented relative to the object;

obtaining, by the local system, information relating to or dependent on position and orientation of the physical element interacting with the object;

sending the information to the remote system;

displaying, on a display of an electronic device of the remote system, the information relating to or dependent on the position and orientation of the physical element interacting with the object;

receiving input at a 6 degree of freedom input device of the remote system for controlling position and orientation of the virtual rendering of the physical element;

controlling the position and orientation of the virtual rendering of the physical element, displayed on the mixed reality headset, relative to the object based on the input received at the input device of the remote system;

wherein the remote system communicates with the local system with latency of 0.5 seconds or less, facilitating alignment of the physical element with the position and orientation of the virtual rendering;

generating, at the local system, a map of the object, and providing haptic feedback at the input device of the remote system, based on a relationship between the physical element and the map of the object wherein generating the map comprises generating a mesh or generating a depth map of constraints that the object is subject to.

11. A method of interaction with an object comprising:

establishing communication between a local system and a remote system located remote from the object;

displaying on a mixed reality headset of the local system, a virtual rendering of a physical element positioned and oriented relative to the object;

obtaining, by the local system, information relating to or dependent on position and orientation of the physical element interacting with the object;

sending the information to the remote system;

displaying, on a display of an electronic device of the remote system, the information relating to or dependent on the position and orientation of the physical element interacting with the object;

receiving input at a 6 degree of freedom input device of the remote system for controlling position and orientation of the virtual rendering of the physical element;

controlling the position and orientation of the virtual rendering of the physical element, displayed on the mixed reality headset, relative to the object based on the input received at the input device of the remote system;

wherein the remote system communicates with the local system with latency of 0.5 seconds or less, facilitating alignment of the physical element with the position and orientation of the virtual rendering, detecting a local applied force by the physical element interacting with the object, determining a remote applied force based on the input received at the input device and comparing the local applied force to the remote applied force and displaying comparison information utilizing the mixed reality headset.

12. The method of claim 11, comprising offsetting, by the mixed reality headset, the virtual rendering by an amount and in a direction based on an impedance value of the object, estimated using the local applied force and position of the physical element relative to the object.

13. The method of claim 11, wherein the physical element comprises an ultrasound probe and wherein obtaining, by the local system, information relating to or dependent on position and orientation comprises obtaining one or both of a visual image of the ultrasound probe interacting with the object and an ultrasound image.

\*  \*  \*  \*  \*